| United States Patent [19] | [11] Patent Number: 4,711,904 |
| Luzzi et al. | [45] Date of Patent: Dec. 8, 1987 |

[54] METHOD OF TREATING SKIN DISORDERS

[76] Inventors: Louis A. Luzzi; Joyce K. Luzzi, both of 165 Sakonnet Blvd., Narragansett, R.I. 02882

[21] Appl. No.: 893,049

[22] Filed: Aug. 4, 1986

[51] Int. Cl.⁴ ............................................. A61K 31/36
[52] U.S. Cl. ...................................................... 514/464
[58] Field of Search ............... 514/171, 172, 174, 177, 514/464

[56] References Cited

U.S. PATENT DOCUMENTS 4,082,881  4/1978  Chen et al. ........................ 514/177

OTHER PUBLICATIONS

Chem. Abst., 101 (1984) 177540f.

*Primary Examiner*—Stanley J. Friedman
*Attorney, Agent, or Firm*—Salter & Michaelson

[57] ABSTRACT

A method of treating skin disorders comprises the step of applying thereto a composition wherein the main active ingredient comprises dimethyl isosorbide. It has been found that dimethyl isosorbide has a dermal penetrating action which can effectively carry it to the source of a skin disorder and that it has antifungal, antiviral and antibacterial effects which make it effective in the treatment of a wide range of skin disorders.

8 Claims, No Drawings

METHOD OF TREATING SKIN DISORDERS

Background and Summary of the Invention

The instant invention relates to the treatment of skin disorders and more particularly to a method of treating skin disorders by topically applying dimethyl isosorbide thereto.

A number of skin disorders are relatively common with large segments of the population. For example, acne, impetigo, eczema, cellulitis, furuncles, carbuncles, folliculitis, tuberculosis of the skin, seborrhea, psoriasis, alopecia, mange, athlete's foot, herpes, warts and corns are all relatively common skin disorders. Further, while it has been found that some of these skin disorders can be effectively treated with various medications, it has also been found that some skin disorders such as psoriasis and herpes are often relatively persistent and often cannot be readily cured in this or any other heretofore known manner. Accordingly, there is a very definite need for a method which is effective in the treatment of a wide variety of skin disorders, including relatively hard-to-cure skin disorders, such as psoriasis and herpes.

The instant invention provides a highly effective and novel method of treating of a wide variety of skin disorders. More specifically, the instant invention provides a mehtod of treating skin disorders by topically applying thereto a composition wherein the main active ingredient comprises dimethyl isosorbide. In this connection, in accordance with the method, dimethyl isosorbide may be applied in various concentrations, and it may be applied in the form of a composition wherein it is mixed with various other inactive ingredients, such as cream bases, oil bases, or water. It has been found that when dimethyl isosorbide is applied to the skin in accordance with the method, it is operative with a solvent action which enables it to dissolve loose fat in the skin so that it can penetrate through the skin membrane to reach the source of a skin disorder. In addition, it has been found that dimethyl isosorbide has antibacterial, antiviral, antifungal and antihypersensitive effects, and as a result, it can often cure most skin disorders within relatively short periods of time.

While the use of dimethyl isosorbide as a carrier for other active ingredients in the treatment of skin disorders has been heretofore known, it has not been previously known that dimethyl isosorbide itself can be utilized as the main active ingredient in a composition for the treatment of skin disorders. In this connection, Chen et al. U.S. Pat. No. 4,082,881, which represents the closest prior art to the subject invention of which the applicant is aware, teaches a method of treating skin disorders by applying a composition thereto comprising dimethyl isosorbide and various active ingredients, wherein the dimethyl isosorbide functions as a carrier for the active ingredients. However, this patent fails to recognize that dimethyl isosorbide itself can be effectively utilized as an active ingredient in the treatment of skin disorders rather than merely as a carrier. The only other pertinent prior art of which the applicant is aware is disclosed in Luzzi et al. U.S. Pat. No. 4,228,162 which teaches the use of dimethyl isosorbide in a liquid formulation of aspirin. However, this patent also clearly fails to recognize that dimethyl isosorbide can be topically applied as an active ingredient in the treatment of skin disorders.

Accordingly, it is a primary object of the instant invention to provide an effective method of treating a wide variety of skin disorders.

Another object of the instant invention is to provide a method of treating skin disorders with a composition wherein the main active ingredient comprises dimethyl isosorbide.

Other objects, features and advantages of the invention shall become apparent as the description thereof proceeds herein.

Description of the Invention

The method of the instant invention is effective in the treatment of disorders in skin tissue, and it comprises the step of applying a composition to the skin tissues wherein the main active ingredient comprises dimethyl isosorbide. In this connection, the method can be effectively utilized in the treatment of a wide variety of skin disorders, including acne, impetigo, eczema, cellulitis, furuncles, carbuncles, folliculitis, tuberculosis of the skin, seborrhea, psoriasis, alopecia, mange, athlete's foot, herpes, warts, and corns.

It has been found that dimethyl isosorbide can be effectively utilized in the treatment and prevention of a wide variety of skin disorders because it is operative with antibacterial, antiviral, antifungal and dermal penetrating actions. In this regard, it has been found that dimethyl isosorbide can effectively penetrate the skin, because it has the ability to dissolve loose fat in the skin so that it can carry across the skin membrane. In fact, dimethyl isosorbide actually has a solvent action which enables it to effectively reach the source of a skin disorder. It has been further found that dimethyl isosorbide has antifungal, antiviral and antibacterial effects, which make it effective against a wide variety of skin disorders.

Dimethyl isosorbide can be effectively applied to the skin for the treatment of skin disorders in various compositions. More specifically, dimethyl isosorbide can be applied directly to the skin, or it can be applied in a composition comprising virtually any conventional vanishing cream or skin cream base, such as Essex (Schearing Corp. TM) cream, or virtually any conventional water or oil base which is suitable for topical application to the skin. For example, dimethyl isosorbide can be formulated with various petrolem based oils, vegetable oils, or castor oil for use on the skin. In this connection, it has been found that a formulation comprising between 1% and 75% by weight dimethyl isosorbide in a vanishing cream and/or an oily base can be highly effective in the treatment of a wide variety of skin disorders when applied thereto in accordance with the method of the subject invention. Dimethyl isosorbide can also be formulated with various conventional water-soluble bases or even with water itself, as well as with various known pastes and lotions for topical applications in accordance with the method. Dimethyl isosorbide can also be applied to the skin in accordance with the method in a liquid emulsion comprising an aqueous and/or a nonaqueous base and a surfactant, such as a Tween (ICI Americas Inc. TM) or a Span (ICI Americas Inc. TM) surfactant. In this regard, when dimethyl isosorbide is applied to the skin in an emulsion, the dimethyl isosorbide may either be the internal phase or the external phase of the emulsion.

EXAMPLE ONE

A formulation comprising 25 weight percent dimethyl isosorbide and 75 weight percent Essex cream was prepared and applied to the skin of a patient for treating eczema on a knuckle of the patient. Specifically, the dimethyl isosorbide formulation was topically applied to the eczema by rubbing a small quantity of the formulation on the eczema throughout the course of one week. It was found that at the end of the week the eczema had been completely cured.

EXAMPLE TWO

A dimethyl isosorbide formulation comprising 25 weight percent of dimethyl isosorbide and 75 weight percent of Essex cream was applied to a wart on the wrist of a patient over a three-week period. Specifically, the dimethyl isosorbide formulation was applied to the wart every two or three days by rubbing a small quantity of the formulation on the wart. At the end of the threeweek period, the wart was completely gone.

Accordingly, it is seen that the instant invention provides an effective method for the treatment of various skin disorders. In this connection, because dimethyl isosorbide has antiviral, antifungal and antibacterial effects, it can be utilized in the treatment of a wide range of skin disorders. Further, because dimethyl isosorbide has a solvent effect, it can effectively pass through the skin membrane to get to the source of a skin disorder. Hence it is seen that the method of the instant invention represents a significant advancement in the treatment of skin disorders.

As this invention may be embodied in several forms without departing from the spirit or essential characteristics thereof, the present embodiment is therefore illustrative and not restrictive, since the scope of the invention is defined by the appended claims rather than by the description preceeding them, and all changes that fall within the metes and bounds of the claims or that form their functional as well as conjointly cooperative equivalents, are therefore intended to be embraced by these claims.

What is claimed is:

1. A method of treating skin tissue for a skin disorder of a viral, bacterial or fungal nature comprising applying thereto an effective amount of composition wherein the main active ingredient comprises dimethyl isosorbide.

2. The method of claim 1 further characterized in that said composition comprises between 1% and 75% by weight dimethyl isosorbide and between 25% and 95% by weight of a cream base.

3. The method of claim 1 further characterized in that said composition comprises dimethyl isosorbide and water.

4. The method of claim 1 further characterized in that said composition comprises dimethyl isosorbide and an oil base of a type which is suitable for topical application to skin tissue.

5. The method of claim 1 further characterized in that said composition consists essentially of dimethyl isosorbide.

6. The method of claim 1 further characterized in that dimethyl isosorbide is the sole active ingredient in said composition.

7. The method of claim 1 further characterized in that said composition comprises an emulsion comprising dimethyl isosorbide, an oil base and a surfactant of a type which is suitable for topical application to skin tissue.

8. The method of claim 1 further characterized in that said composition comprises an emulsion comprising dimethyl isosorbide, a water base and a surfactant of a type which is suitable for topical application to skin tissue.

* * * * *